（12） United States Patent
Seshimoto et al.

(10) Patent No.: US 7,059,480 B2
(45) Date of Patent: Jun. 13, 2006

(54) CONTINUOUS BLOOD FILTRATION APPARATUS

(75) Inventors: Osamu Seshimoto, Saitama (JP); Kenichiro Yazawa, Saitama (JP)

(73) Assignee: Fuji Photo Film Co., Inc., Kanagawa (JP)

( * ) Notice: Subject to any disclaimer, the term of this patent is extended or adjusted under 35 U.S.C. 154(b) by 0 days.

(21) Appl. No.: 10/674,445

(22) Filed: Sep. 30, 2003

(65) Prior Publication Data

US 2004/0060859 A1 Apr. 1, 2004

Related U.S. Application Data

(63) Continuation of application No. 09/642,528, filed on Aug. 18, 2000, now abandoned, which is a continuation of application No. 09/287,424, filed on Apr. 7, 1999, now abandoned.

(30) Foreign Application Priority Data

Apr. 10, 1998 (JP) .................................. 10/099426

(51) Int. Cl.
*B01F 33/333* (2006.01)

(52) U.S. Cl. ............. 210/406; 210/321.67; 210/321.84; 210/340; 210/390; 210/416.1; 422/65; 422/101; 422/103

(58) Field of Classification Search ................. 422/64, 422/65, 80, 101, 103; 210/321.67, 321.84, 210/340, 390, 406, 416.1

See application file for complete search history.

(56) References Cited

U.S. PATENT DOCUMENTS

| 3,827,386 | A | * | 8/1974 | Faden ........................ 114/91 |
| 4,415,449 | A | * | 11/1983 | Hein .......................... 210/406 |
| 5,262,049 | A | * | 11/1993 | Ferkany ...................... 210/258 |
| 5,602,348 | A | * | 2/1997 | Takakarhu et al. ....... 73/864.81 |
| 5,690,815 | A | * | 11/1997 | Krasnoff et al. ............. 210/97 |
| 6,117,394 | A | * | 9/2000 | Smith ......................... 422/100 |
| 6,225,130 | B1 | * | 5/2001 | Kitajima et al. ............ 436/177 |
| 6,241,947 | B1 | * | 6/2001 | Komatsu et al. ............. 422/67 |
| 6,379,565 | B1 | * | 4/2002 | Guirguis et al. ............ 210/767 |

FOREIGN PATENT DOCUMENTS

| EP | 0 785 012 A1 | * | 7/1997 |
| JP | 11-295301 | * | 10/1999 |

* cited by examiner

*Primary Examiner*—David Sorkin
(74) *Attorney, Agent, or Firm*—Reed Smith LLP

(57) ABSTRACT

This invention provides a continuous blood filtration apparatus capable of filtering a plurality of blood samples continuous by using blood filter units to prepare plasma or serum samples in a short period, which comprises, a conveyor conveying a plurality of blood reservoirs each of which contains a blood sample and in which a suction nozzle of a blood filter unit has been put, a manifold connected to a suction line, couples of a valve and a connector for connecting the manifold to the blood filter unit provided on the end of each branch of the manifold, and a mechanism of moving the blood reservoirs in vertical direction.

9 Claims, 6 Drawing Sheets

CONTINUOUS BLOOD FILTRATION APPARATUS

CROSS-REFERENCE TO RELATED APPLICATIONS

This is a continuation of application Ser. No. 09/642,528, filed 18 Aug. 2000, now abandoned, which is a continuation of application Ser. No. 09/287,424, filed 7 Apr. 1999, now abandoned.

BACKGROUND OF THE INVENTION

This invention relates to a continuous blood filtration apparatus capable of treating a plurality of samples continuously.

The type or concentration of blood components, such as metabolites, proteins, lipids, electrolytes, enzymes, antigens, and antibodies, is measured, in general, using a plasma or serum sample obtained by centrifuging whole blood. However, centrifuging cannot be incorporated into a line, and takes labor and time. Particularly, centrifuging is unsuitable for an urgent case of measuring a small number of samples promptly and on site inspection, because of requiring a centrifuge and electricity. Therefore, the separation of serum from whole blood by has been investigated.

Several filtration methods using glass fiber filter have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except for a specialized test, such as blood sugar.

On the other hand, the inventors developed a blood filter unit composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1)

Another blood filter unit composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012 A1).

However, since the blood filter units already developed filter blood one by one, it is desired to develop a continuous filtration apparatus for filtering many blood samples successively using the blood filter units in order to improve working efficiency.

SUMMARY OF THE INVENTION

An object of the invention is to provide a continuous blood filtration apparatus capable of filtering a plurality of blood samples continuous by using blood filter units to prepare plasma or serum samples in a short period.

As a result of investigating in order to solve the above problems, the inventors have developed a continuous blood filtration apparatus which comprises, a conveyor conveying a plurality of blood reservoirs each of which contains a blood sample and in which a suction nozzle of a blood filter unit has been put, a pipe connected to a suction line and provided with a connector for connecting the pipe to the blood filter unit, and a mechanism of moving the blood reservoirs in vertical direction.

They also have developed a continuous blood filtration apparatus which comprises, a conveyor conveying a plurality of blood reservoirs each of which contains a blood sample and in which a suction nozzle of a blood filter unit has been put, a manifold connected to a suction line, couples of a valve and a connector for connecting the manifold to the blood filter unit provided on the end of each branch of the manifold, and a mechanism of moving the blood reservoirs or the connector in vertical direction which also have achieved the above object.

Figure 1:
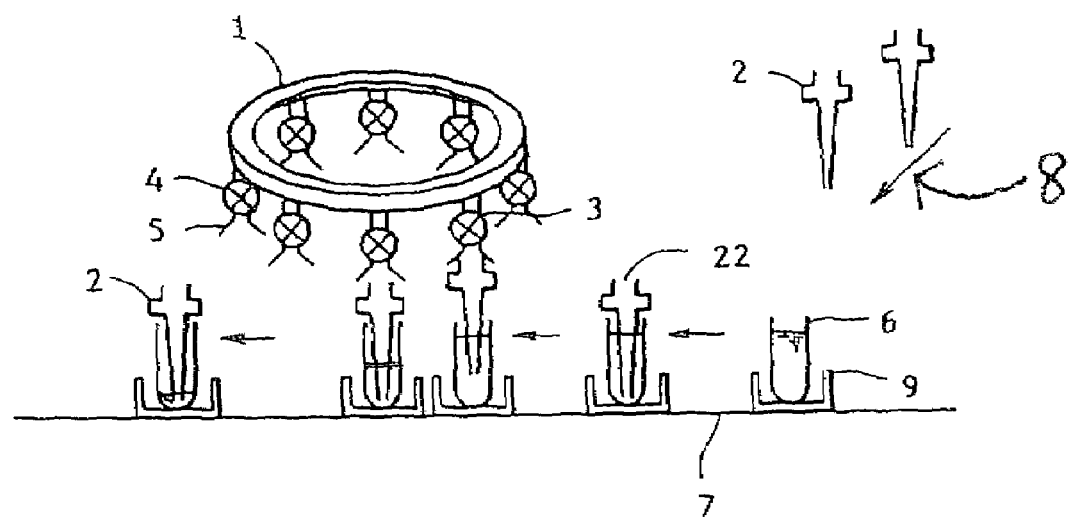
FIG. 1 is a schematic illustration showing the construction of a continuous blood filtration apparatus which embodies the invention.

1 . . . Manifold
2 . . . Blood filter unit
3 . . . Branch
4 . . . Valve
5 . . . Connector
6 . . . Vacuum blood collecting tube
7 . . . Conveyor
8 . . . Feeder
9 . . . Rack
10 . . . Holder body
11 . . . Glass fiber filter chamber
12 . . . Microporous membrane chamber
13 . . . Inclined portion
14 . . . Flange
15 . . . Glass fiber filter-placing portion
16 . . . Funnel-shaped disc portion
17 . . . Blood inlet
19 . . . Step portion
20 . . . Cap
21 . . . Outer wall
22 . . . Inner wall, suction port
23 . . . Cup
24 . . . Flange
25 . . . Rib
26 . . . Projection
27 . . . Filtrate passage
28 . . . Pent roof 29 . . . Discharge port
30 . . . Glass fiber filter
40 . . . Polysulfone microporous membrane
50 . . . Intermediate cap
51 . . . Filtrate receiver
52 . . . Discharge port
53 . . . Tapered wall
54 . . . Step portion
55 . . . Gap
56 . . . Projection
57 . . . Flange
58 . . . Plug
59 . . . Flange
60 . . . Upper cap
61 . . . Opening
62 . . . Flange
63 . . . Restraining member
64 . . . Disc
65 . . . Leg
70 . . . Clamp
71 . . . Connection port
72 . . . Suction line

DETAILED DESCRIPTION OF THE INVENTION

In the apparatus of the invention, it is preferable to incorporate a buffer tank between the suction line and the manifold. The buffer tank has a closed structure, and the inside is made reduced pressure conditions by connecting a suction pump. The buffer tank has a capacity capable of continuing filtration of other blood filter units, even while a part, usually one, of the sucking blood filter units are changed.

The manifold connects between the suction line and respective blood filter units, and is composed of a main pipe and branches. The main pipe may be either fixed or moved vertically in a linear form of rectangular box or straight pipe, or rotated in a form of circular box or ring pipe. In the case of ring-shaped, a connecting port to the suction line is provided at the center, and the ring-shaped main pipe is connected thereto through connecting pipe(s). The rotation of the manifold is continuous or intermittent.

A valve and a connector are provided at the end of each branch. The valve opens upon attaching the blood filter unit and closes upon detaching it. The valve may be any type capable of being accommodated thereto, such as in the cock type, the push valve type, the butterfly valve type, the disc valve type, the gate valve type, the ball valve type, the bell center valve type, or the like in structural viewpoint, and the mechanical valve type, the electromagnetic valve type, or the like in working viewpoint. In the mechanical valve type, when the attaching (detaching) direction of the blood filter unit conforms to the opening (closing) direction of the valve, the valve can be opened or closed by the movement of the connector by connecting the valve body with the connector through a connecting rod or the like. As another means, the valve body can be returned by the suction of the suction line upon the detaching of the blood filter unit without connecting the valve body with the connector. In the case that the attaching (detaching) direction of the blood filter unit is opposite to the opening (closing) direction of the valve, the direction can be changed by using a lever mechanism. In the case of using an electromagnetic valve, the electromagnetic valve can be actuated by a switch which is changed over by the movement of the blood filter unit.

The connector is joined to the suction port of the blood filter unit to connect it to the suction line through the manifold. It is preferable to attach a flexible material or elastic material, such as rubber, to the catching part of the connector to the suction port of the blood filter unit so as to ensure airtight ability. It is also preferable that the connector is made movable in the vertical direction so as to facilitate attaching and detaching of the blood filter unit. As the means for providing the vertical movement, there are to render the connection of the connector to a branch of the manifold through a sliding structure, to use a flexible bellows, and the like. It is also possible to incline the manifold ring, and the connector is connected to the suction port of the blood filter unit near the lowest part of the manifold ring. In this case, each connector is not necessary to be movable. The manifold may be a flexible tube made of rubber, plastic or the like, or a combination of a rigid material, such as metal or glass, and a flexible material.

In the blood filtration apparatus of the invention, it is possible to use a pipe connected to a suction line and provided with the connector, wherein filtration can be carried out by reciprocating movement of the pipe.

The conveyor conveys the blood reservoirs. When the blood reservoirs are held by racks or the like, the conveyor is composed of a endless belt, chain or the like. Instead, racks for holding the blood reservoir can be mounted to the conveyor. The movement of the conveyor may be either intermittent or continuous. When the manifold is rotated, the movement of the conveyor can be synchronized with the manifold.

The form of the rack is disc, square plate, band or the like. The rack holds and positions the blood filter unit so as to be attachable to and detachable from the connector of each branch of the manifold. The simplest structure of the rack is a plate or box having a single or plural openings into which the blood filter unit is inserted to engage the flange to the periphery of the opening.

Although the shape of the reservoir is not restricted, for example, a commercial vacuum blood collecting tube can be used as it is. In this case, an apparatus for taking the blood filter unit out of the rack and putting the blood filter unit in the vacuum blood collecting tube is provided in addition to the rack. When the blood reservoir includes the blood filter unit, the above apparatus is not necessary.

The moving mechanism of the blood reservoirs in the vertical direction is to hold the blood reservoir or a rack, in the case that the blood reservoir is held thereby, to move it in the vertical direction. It is preferable to hold the blood filter unit to move it in the vertical direction in addition to the blood reservoir or the rack.

The blood filter unit is composed of a blood filtering material and a holder which accommodates the blood filtering material and has a blood inlet and a filtrate outlet.

Although the type of the blood filtering material is not limited, in the filtering material of the invention, it is thought that the filter material to be used does not trap blood cells only by the surface, but catches to remove blood cells gradually by entangling at first large blood cell components and then smaller blood cell components in the space structure with permeating in the thickness direction in total of the filtering material, called the volumetric filtration. Preferable blood filtering material are glass fiber filter, microporous membrane, and the like, and a combination of glass fiber filter and microporous membrane is particularly preferred.

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 μm preferably 1 to 5 μm. By treating the surface of glass fiber with hydrophilic polymer as disclosed in Japanese Patent KOKAI Nos. 2-208565, 4-208856, filtration proceeds faster and more smoothly. Lectin or other reactive reagent or modifier may be incorporated into glass fiber, or glass fiber may be treated therewith. Two or more glass fiber filters may be superimposed.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 μm or more, preferably about 0.3 to 5 μm, more preferably about 0.5 to 4.5 μm, particularly preferably about 1 to 3 μm. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, etc. The surface of the membrane may be hydrolyzed or may be rendered hydrophilic by a hydrophilic polymer or an activating agent.

Preferable microporous membranes are polysulfone membrane, cellulose acetate membrane and the like, and particularly preferred one is polysulfone membrane. In the blood filtering material of the invention, the glass fiber filter is located on the blood inlet side and the microporous membrane in located on the filtrate outlet side. The most preferable blood filtering material is a combination of the glass fiber filter and polysulfone membrane superimposed in this order from the blood inlet side.

Respective layers may be integrated by joining each other using partially disposed (e.g. spots) adhesive, according to disclosures in Japanese Patent KOKAI Nos. 62-138756-8, 2-105043, 3-16651, etc.

The quantity of whole blood filterable by this system is greatly influenced by the void volume existing in glass fiber filter and the volume of blood cells in the whole blood. When the density of the glass fiber filter is high (pore size to retain particles is small), erythrocytes are trapped in the vicinity of glass fiber filter surface, voids in the glass fiber filter are clogged in a very thin region from the surface, and accordingly, filtration does not proceed thereafter. As a result, recovered plasma volume by filtration is small. On that occasion, when the filter material is sucked by stronger suction in order to increase recovered plasma volume, blood cells are destroyed, i.e. hemolyzed. That is, the filtration becomes similar to surface filtration, and utilization rate of void volume of the filter is low.

As an indicator corresponding to void volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking at a constant pressure. The water permeation speed is filtrate volume per unite area and time, and expressed by ml/sec.

For example, glass fiber filter 20 mm in diameter is put in a filter unit, and a 100 ml syringe containing 60 ml water is connected to the top of the filter unit. Water flows down naturally, and volume of water passing through the glass filter from 10 sec to 40 sec after starting is measured as the water permeation volume, and the water permeation speed per unit area is calculated from it.

Glass fiber filters particularly suitable for plasma separation are having a water permeation speed of about 1.0 to 1.3 ml/sec, and illustrative of the glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 g/cm$^3$) on a nylon net. The glass fiber filter thus prepared shows good plasma separating ability.

A suitable thickness of the glass fiber filter varies according to the plasma volume to be recovered and density (void content) and area of the glass fiber filter. A necessary amount of plasma for analyzing plural items using dry analytical elements is 100 to 500 μl. In practical viewpoint, a glass fiber filter having a density of about 0.02 to 0.2 g/cm$^3$ and an area of 1 to 5 cm$^2$ is suitable. In this case, a suitable thickness of the glass fiber filter is about 1 to 10 mm, preferably about 2 to 8 mm, more preferably about 4 to 6 mm. The above thickness can be made by superposing 1 to 10 sheets, preferably 2 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

In the case of blood filter unit, the blood filtering material is placed in a holder having a blood inlet and a filtrate outlet. The holder is, in general, formed of a body accommodating the blood filtering material and a cap, and each of them is provided with at least one aperture. One is used as the blood inlet, and the other is used as the filtrate outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which accommodates the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material. Although the actual volume is designed depending on the necessary quantity of plasma or serum, the volume is about 0.5 to 2.5 ml, usually about 0.6 to 2.2 ml.

Besides, it is preferable that the periphery of the blood filtering material is closely fitted to the wall of the filter chamber so as not to form a bypass of whole blood without passing the filtering material. However, leakage of blood cells to the degree capable of trapping by microporous membrane is allowable.

The blood filter unit is made into a closed structure except the blood inlet and the plasma outlet by attaching a cap to the holder body.

As the material of the holder, thermoplastic or thermosetting plastics are preferable. Illustrative of the plastics are general-purpose polystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss.

The suction nozzle is connected to the blood inlet of the holder, and sucks blood. The suction nozzle may be integrated with or separated from the holder. In the case of separated, it is enough that the nozzle is joined in an airtight state, and the joining means may be any means, such as adhesion, fusion, screwing, fitting, or the like.

EXAMPLE

An example of the continuous blood filtration apparatus is shown in FIG. 1.

In the apparatus, the manifold 1 is ring-shaped, and branches 3 to which blood filter units 2 are connected are provided downward from the underside of the manifold main pipe at regular intervals. Each branch 3 is provided with a valve 4 in the middle of the branch and a connector 5 at the lower end. Connector 5 is made movable in the vertical direction as shown by dotted lines A to facilitate attaching and detaching of blood filter units 2 as shown in FIG. 1 a.

Figure 1A:
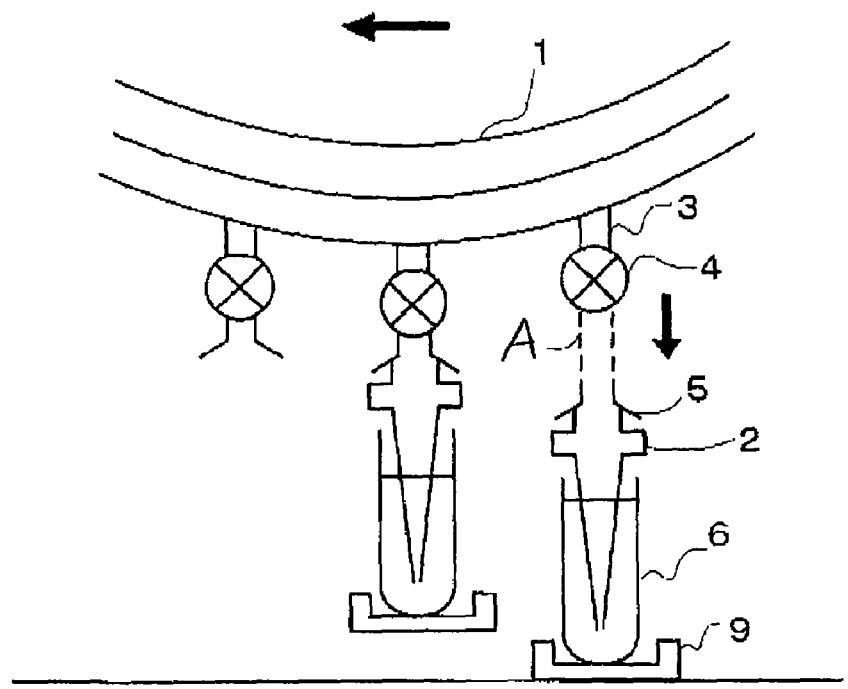
FIG. 1a is an exploded schematic illustration of FIG. 1.
Figure 1B:
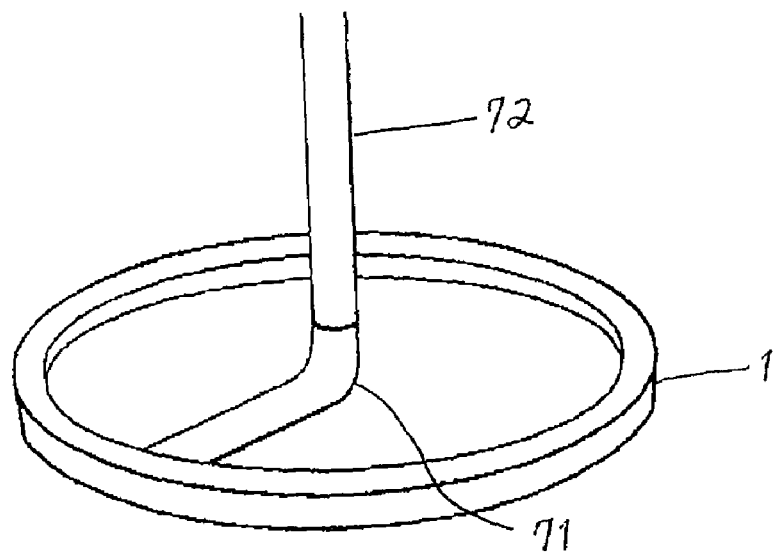
FIG. 1b is plan view of a suction line connected to the manifold of FIG. 1.

FIG. 1b shows that in the case of a ring shaped manifold 1, a connecting port 71 to a suction line 72 is provided at the center.

Vacuum blood collecting tubes 6 containing blood sample are conveyed intermittently by a conveyor from the right side in the figure, and the blood filter units 2 supplied by a blood filter unit feeder 8 are put in the vacuum blood collecting tubes 6 one by one. When the vacuum blood collecting tube reaches just under the manifold 1, the connector 5 descends to catch the suction port 22. The valve 4 opens to suck blood sample, and blood filtration is carried out. Each rack 9 is retained by a retainer (not illustrated), and travels in accordance with the movement of the manifold 1. During slow rotation of the manifold 1, blood filtration is finished. Then, the connector 5 releases the suction port 22 and ascends, and the valve 4 is closed. The vacuum blood collecting tube 6 returns to the conveyor 7, and further advances.

Thus, blood is sucked successively from the blood collecting tubes 6 delivered successively by the suction of each branch 3 of the manifold, and blood filtration is carried out.

Figure 2:
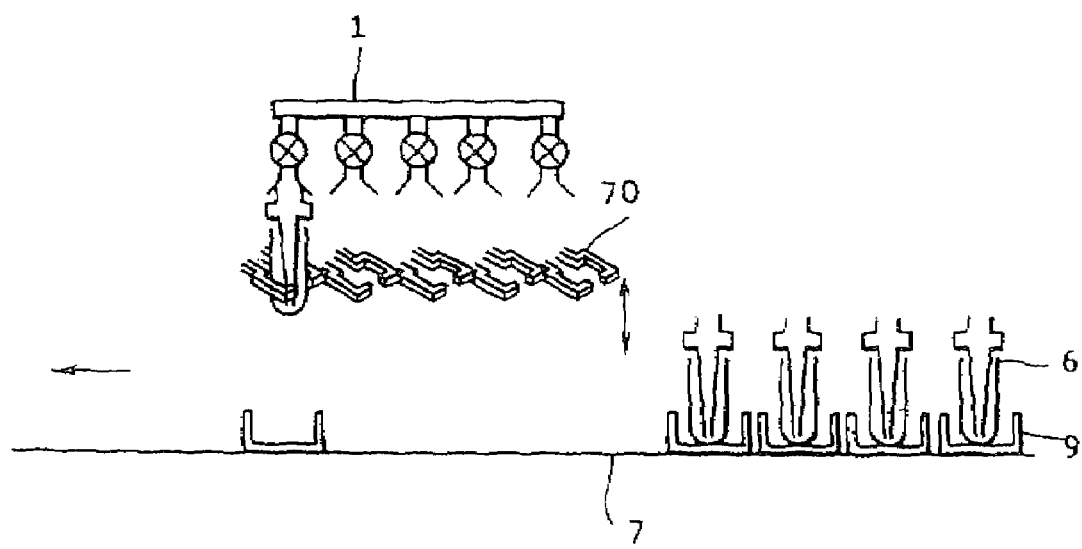
FIG. 2 is a schematic illustration showing the construction of another continuous blood filtration apparatus which also embodies the invention.

Another example of the continuous blood filtration apparatus is shown in FIG. 2.

The manifold 1' of the apparatus is a long rectangular box. When a vacuum blood collecting tube 6 conveyed by the conveyor 7 comes under a vacant branch 3 discriminated by a sensor or bar code, the rack 9 is grasped by a clamp 70 to ascend. Then, the suction port 22 of the blood filter unit 2 is connected to the branch 3, and blood filtration is carried out. After blood filtration is finished, the blood filter unit 2 is separated from the branch 3, and returns to the conveyor 7, and further advances.

Figure 3:
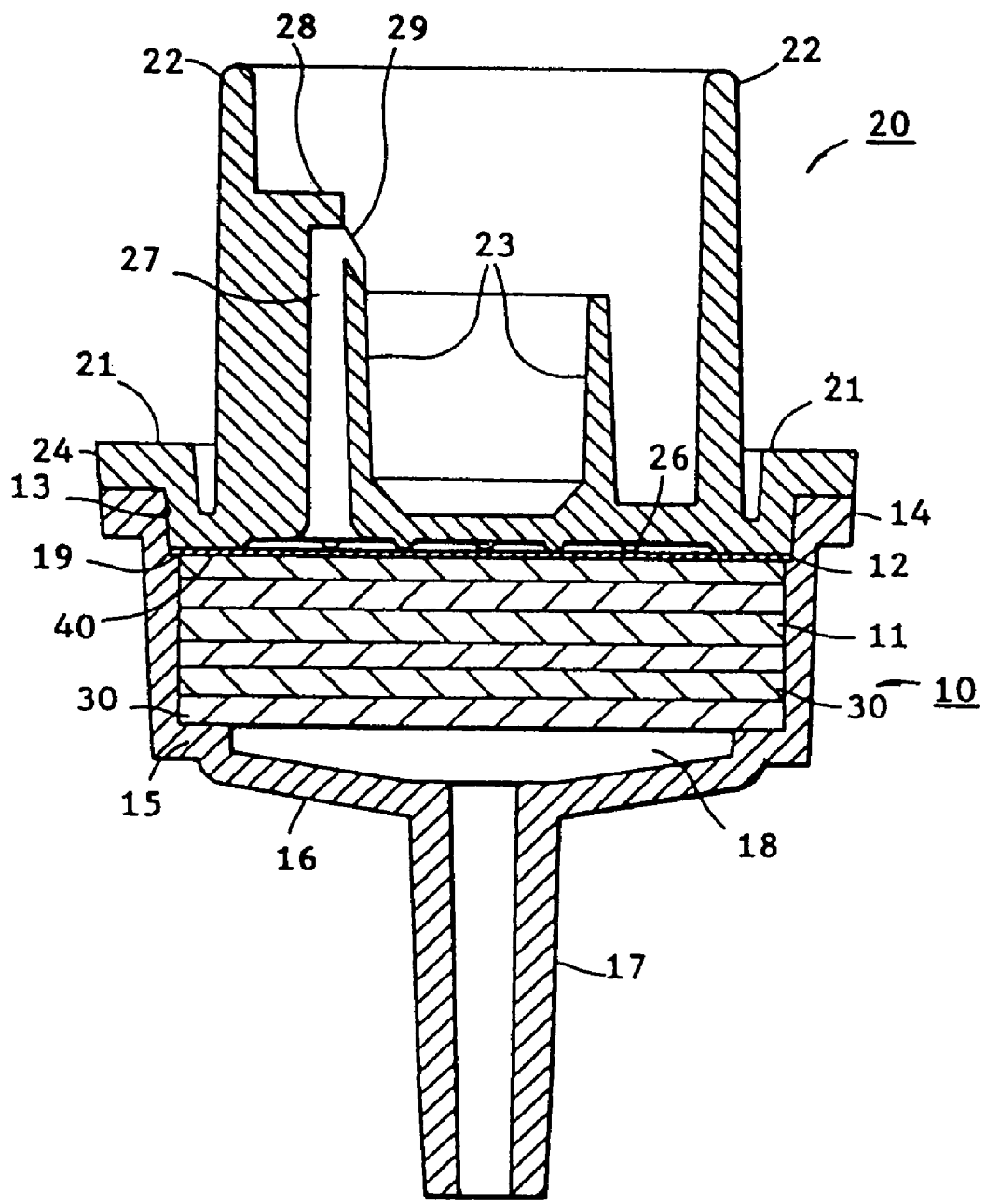
FIG. 3 is a longitudinal section of a blood filter unit used in the invention.
Figure 4:
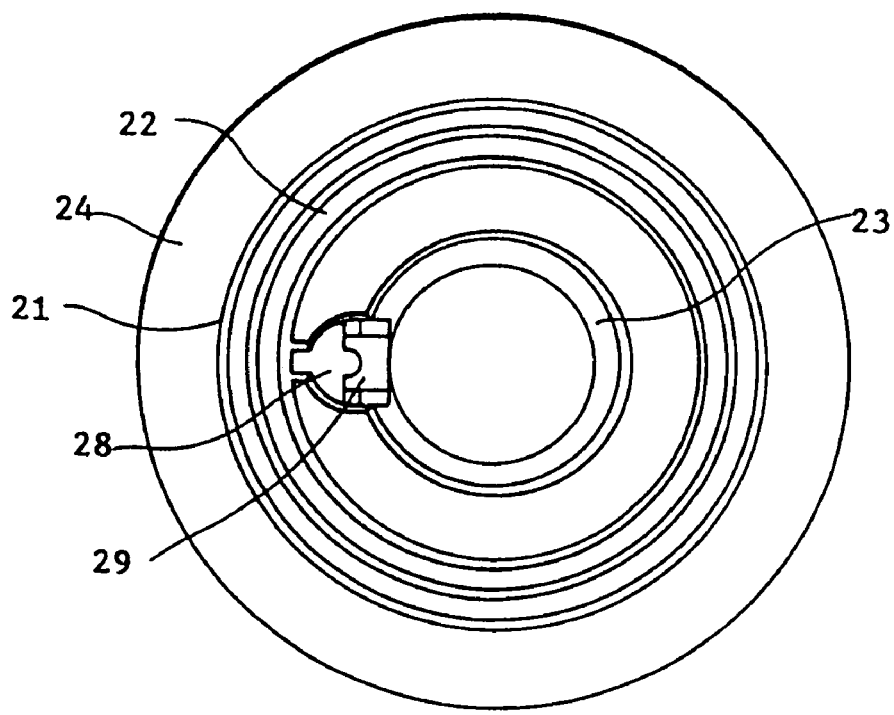
FIG. 4 is a plan view of the cap of the unit.
Figure 5:
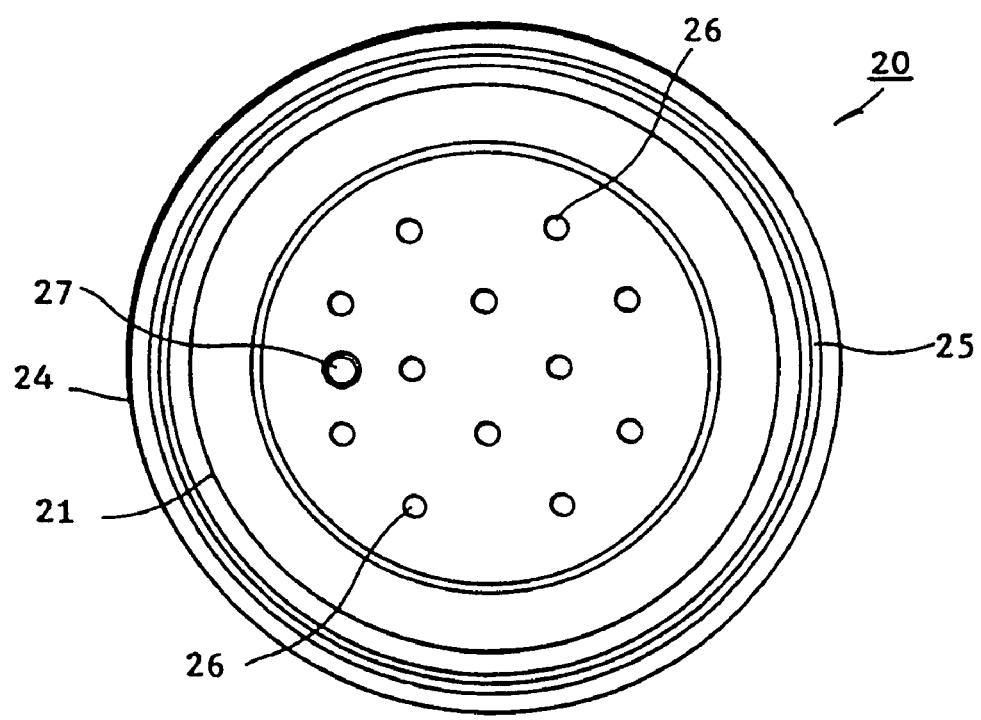
FIG. 5 is a bottom view thereof.

An example of the blood filter unit used in the apparatus of the invention is shown in FIGS. 3–5.

The blood filter unit is, as shown in FIG. 3, composed of a holder consisting of a holder body 10 and a cap 20 and blood filtering material consisting of a glass fiber filter 30 and a microporous membrane 40.

The holder body 10 is made of high-impact polystyrene resin, and has a glass fiber filter chamber 11 for containing the glass fiber filter 30 and a microporous membrane chamber 12 for containing a polysulfone microporous membrane as the microporous membrane 40 above the glass fiber filter chamber 11. The microporous membrane has a diameter greater than the glass fiber filter chamber, and the periphery of the microporous membrane 40 is nipped by the step portion 19 formed on the boundary between the glass fiber filter chamber 11 and the microporous membrane chamber 12 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the other hand, the bottom of the holder body 10 is in the form of a shallow funnel, and a step portion is formed as a glass fiber filter-placing portion 15 at the periphery of the funnel-shaped disc portion 16. A nozzle-shaped blood inlet 17 is formed downward as the supply port of liquid to be filtered at the center of the funnel-shaped disc portion 16. A suction nozzle (not illustrated) is fitted to the nozzle-shaped blood inlet 17. The glass fiber filter-placing portion 15 also functions as a spacer which separates the glass fiber filter 30 from the bottom and forms a space 18 for spreading the liquid to be filtered over the whole surface of the glass fiber filter 30.

The cap 20 has an outer wall 21 and an inner wall 22 formed concentrically and a cup 23 as the receiver of the filtrate. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined 13 in a sealing state. A flange 24 is formed outward at the periphery of the outer wall 21, and the flange 24 is bonded to the flange 14 of the holder body 10 by ultrasonic welding. As shown in FIG. 5, a rib 25 is formed on the underside of the flange 24 so as to concentrate the ultrasonic energy there to be bonded to each other to ensure sealing. The rib 25 disappears after bonding.

As shown in FIG. 5, twelve projections 26 are formed at the bottom of the cap 20 at almost regular intervals. The projections 26 prevent the polysulfone microporous membrane 40 from adhering to the bottom.

A chimney-shaped filtrate passage 27 is formed upward penetrating the bottom of the cap 20, and a pent roof 28 is formed horizontally at the upper end of the filtrate passage 27 so as to prevent spouting of the filtrate. The pent roof 28 has the form of a combination of two half circles, as shown in FIG. 4, and the periphery of the large half circle conforms to the periphery of the filtrate passage 27. The discharge port 29 of the filtrate is provide obliquely at the upper end of the filtrate passage 27, and has the form of a lower half ellipse.

The above blood filter unit has a diameter of the glass fiber filter chamber 11 of 20.1 mm and a depth thereof of 5.9 mm, a diameter of the microporous membrane chamber 12 of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the cup 23 of 7.5 mm. The glass fiber filter 30 consists of six glass fiber filter sheets each having a diameter of 20.0 mm and a thickness of 0.91 mm, and the microporous membrane consists of one polysulfone microporous membrane having a diameter of 20.9 mm and a thickness of 150 μm.

Figure 6:
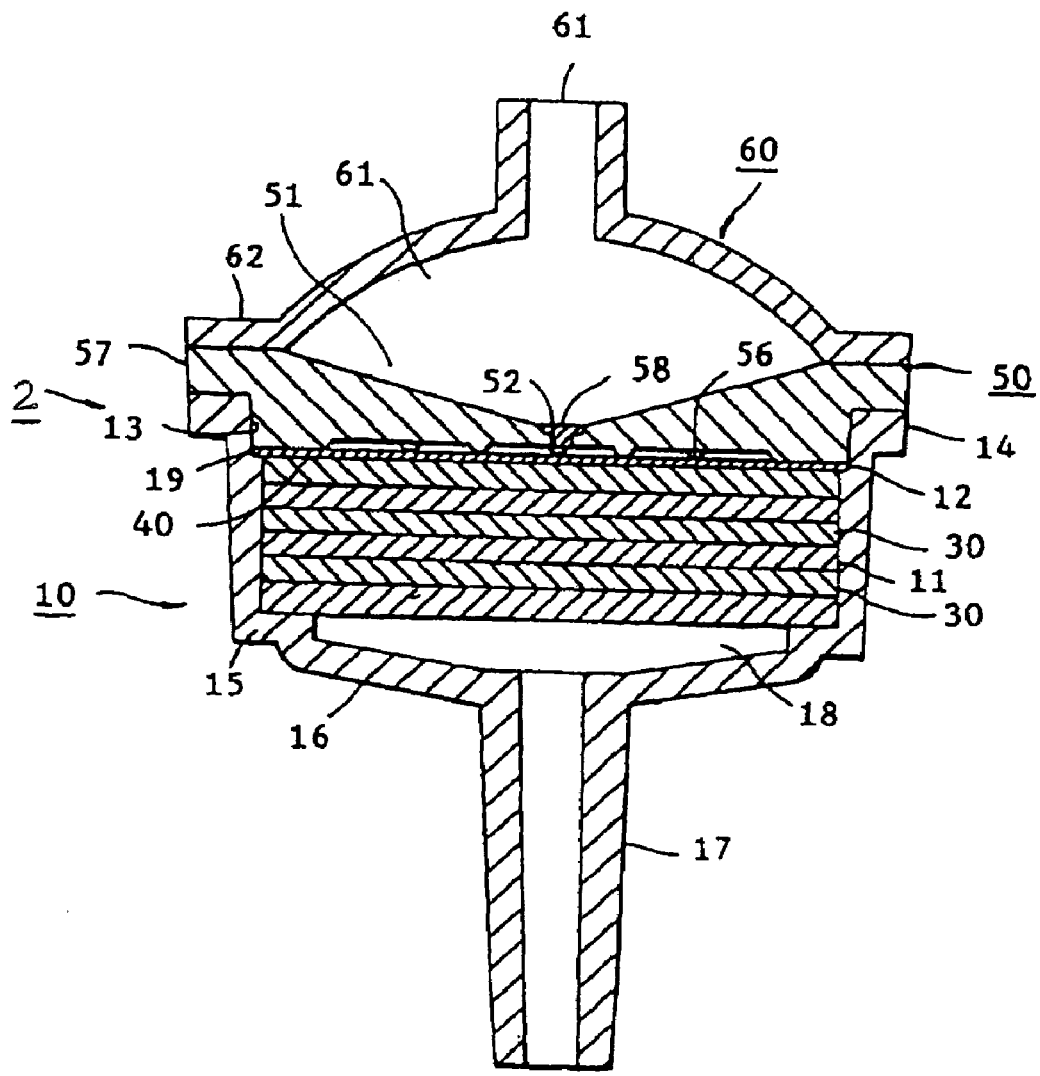
FIG. 6 is a longitudinal section of another blood filter unit used in the invention.
Figure 7:
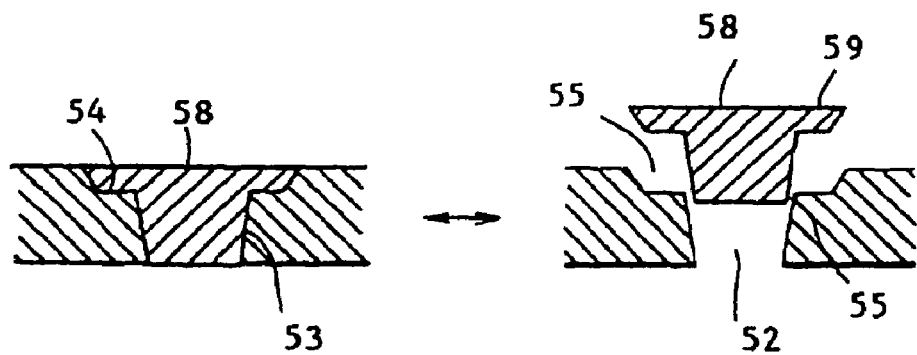
FIG. 7 is a partial section of the intermediate cap of the unit illustrating the opening mechanism of the intermediate cap.
Figure 8:
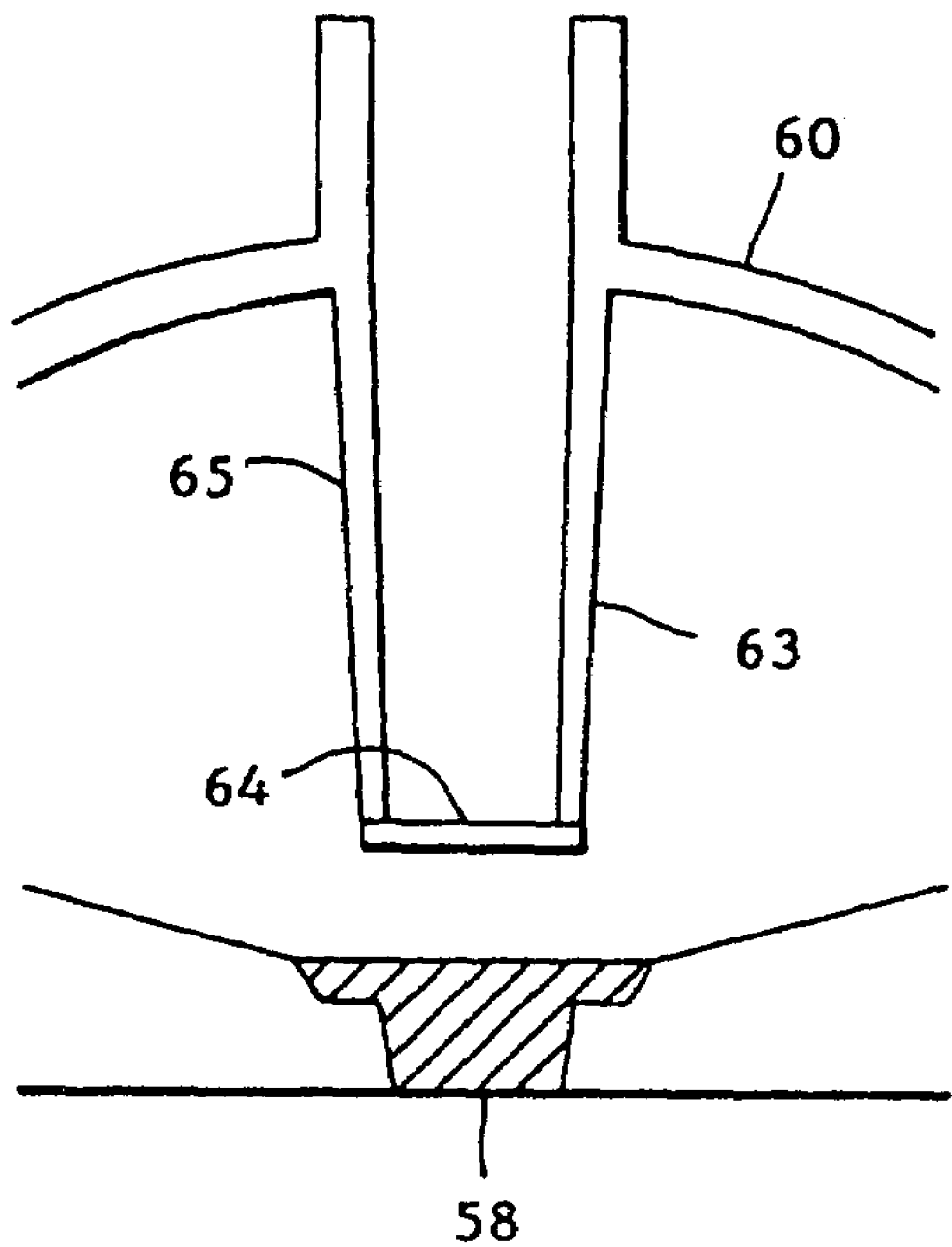
FIG. 8 is a partial section of the intermediate cap and an upper cap to which a restraining member of the plug is formed on the upper cap.

Another example of the blood filter unit applicable to the invention is shown in FIGS. 6–8.

The blood filter unit is, as shown in FIG. 6, composed of a holder body, an intermediate cap 50 fixed to the upper part of the holder body 10 and an upper cap 60 fixed further thereonto.

The holder body 10 is the same as shown in FIG. 3.

The upper side of the intermediate cap 50 becomes a shallow cone-shaped filtrate receiver 51 deepest at the center, and a discharge port 52 of the filtrate is provided at the center. The peripheral wall of the discharge port 52 is tapered, as shown in FIG. 7, and a step portion 54 is formed at the upper part of the tapered wall 53. The discharge port 52 is closed by fitting a rubber plug 58 having a shape just agreeing with the discharge port 52 and a specific gravity of about 1.1. As shown on the right side in FIG. 7, the plug 58 opens by the pressure added upon filtration to form a gap 55 for passing filtrate. The passage of the filtrate is curved by the step portion 54 of the discharge port 52 and the flange 59 of the plug 58, and spouts obliquely upward. 12 projections 56 are formed at the bottom of the intermediate cap 50 at almost regular intervals. The projections 56 prevent the polysulfone microporous membrane 40 from adhering to the bottom. A flange 57 is formed at the periphery of the intermediate cap 50 which is bonded to the flange 14 of the holder body 10 by welding.

The upper cap 60 is in a form of reversed bowl provided with an opening 61 at the center for the suction upon blood filtration and as the entrance of a suction nozzle (not illustrate) of an analyzer upon analysis of the filtrate. A flange 62 is formed at the periphery which is bonded to the flange 57 of the intermediate cap 50 by welding.

FIG. 8 illustrates a restraining member 63 which restricts the ascending limit of the plug 58 so as not to escape. The restraining member 63 is formed of a disc 64 and two legs 65 connecting the disc 64 to the upper cap 60.

The invention claimed is:

1. A continuous blood filtration apparatus for separating plasma or serum from whole blood, the apparatus comprising:
    blood filter units, each comprising a suction nozzle, a filter chamber communicating with the suction nozzle and having a volume of 0.5 to 2.5 ml, a suction port communicating with the filter chamber and a glass fiber filter in the filter chamber;
    blood collecting tubes for containing whole blood and having an opening for receiving and holding a blood filter unit placed through the opening such that the opening of the suction nozzle is below a surface of whole blood contained in the collecting tubes;
    a manifold connected to a suction line, the manifold having a plurality of branches, each branch having a valve and a connector for connecting an end of each branch to a suction port of a blood filter unit;
    a conveyor for conveying blood collecting tubes containing a blood filter unit to a connector such that the suction port of the blood filter unit is facing the connector; and
    a means for moving the blood collecting tube containing the blood filter unit of which the suction port is facing the connector or the connector in a vertical direction to connect the suction port of the blood filter unit with the connector such that when a vacuum is applied through the manifold, blood is drawn from the blood collecting tube into the blood filter unit to filter the blood through the glass fiber and for moving the blood collecting tube or the connector to release the suction port from the connector after blood filtration is finished.

2. The apparatus of claim 1, wherein the manifold has linear form, and is fixed or moved vertically.

3. The apparatus of claim 1, wherein the manifold has a ring form, and is rotated.

4. The apparatus of claim 1, wherein the connector is movable in the vertical direction.

5. The apparatus of claim 1, wherein each blood collecting tube is held by a rack.

6. The apparatus of claim 1, which includes a grasp means for elevating each blood collecting tube to connect each blood filter unit to the connector.

7. The apparatus of claim 1, wherein each blood filter unit filters blood in an upward direction.

8. The apparatus of claim 1, wherein each blood filter unit further comprises a filtrate receiver placed above and communicating with the filter chamber.

9. The apparatus of claim 1, wherein the connector includes a flexible or elastic material where it contacts the suction port in order to ensure an airtight connection.

* * * * *